(12) United States Patent
Chi et al.

(10) Patent No.: US 8,759,521 B2
(45) Date of Patent: Jun. 24, 2014

(54) PANCHROMATIC PHOTOSENSITIZERS AND DYE-SENSITIZED SOLAR CELL USING THE SAME

(75) Inventors: Yun Chi, Hsinchu (TW); Kellen Chen, Hsinchu (TW); Yi-Huan Hong, Hsinchu (TW); Pi-Tai Chou, Taipei (TW); Bo-So Chen, Taipei (TW)

(73) Assignee: National Tsing Hua University, Hsinchu (TW)

( * ) Notice: Subject to any disclaimer, the term of this patent is extended or adjusted under 35 U.S.C. 154(b) by 241 days.

(21) Appl. No.: 13/354,010

(22) Filed: Jan. 19, 2012

(65) Prior Publication Data

US 2012/0111410 A1    May 10, 2012

Related U.S. Application Data

(63) Continuation-in-part of application No. 12/495,044, filed on Jun. 30, 2009, now abandoned.

(30) Foreign Application Priority Data

Apr. 10, 2009   (TW) ................................ 98111934 A (51) Int. Cl.
*C07F 15/00* (2006.01)
*H01L 31/042* (2014.01)

(52) U.S. Cl.
CPC ........... *C07F 15/0046* (2013.01); *Y02E 10/542* (2013.01)
USPC ................................ 546/2; 548/101; 136/263

(58) Field of Classification Search
CPC .................... C07F 15/0046; Y02E 10/542
USPC .................... 546/2; 548/101; 136/263
See application file for complete search history.

(56) References Cited

PUBLICATIONS

Sens et al., "A New Ru Complex Capable of Catalytically Oxidizing Water to Molecular Dioxygen" Journal of the American Chemical Society, (Mar. 8, 2004), pp. 7798-7799, vol. 126, No. 25.
Wu, et al., "Synthesis and Characterization of Metal Complexes Possessing the 5-(2-Pyridyl) Pyrazolate Ligands: The Observation of Remarkable Osmium-Induced Blue Phosphorescence in Solution at Room Temperature", Organometallics, American Chemical Society, (Jul. 13, 2003), pp. 4938-4946, vol. 22.

*Primary Examiner* — Joseph Kosack
(74) *Attorney, Agent, or Firm* — Muncy, Geissler, Olds & Lowe, P.C.

(57) ABSTRACT

Panchromatic photosensitizers having a Formula of $ML_1L_2X$ were synthesized, wherein M represents ruthenium atom; X represents a monodentate anion; $L_1$ is heterocyclic bidentate ligand having one of formulae listed below:

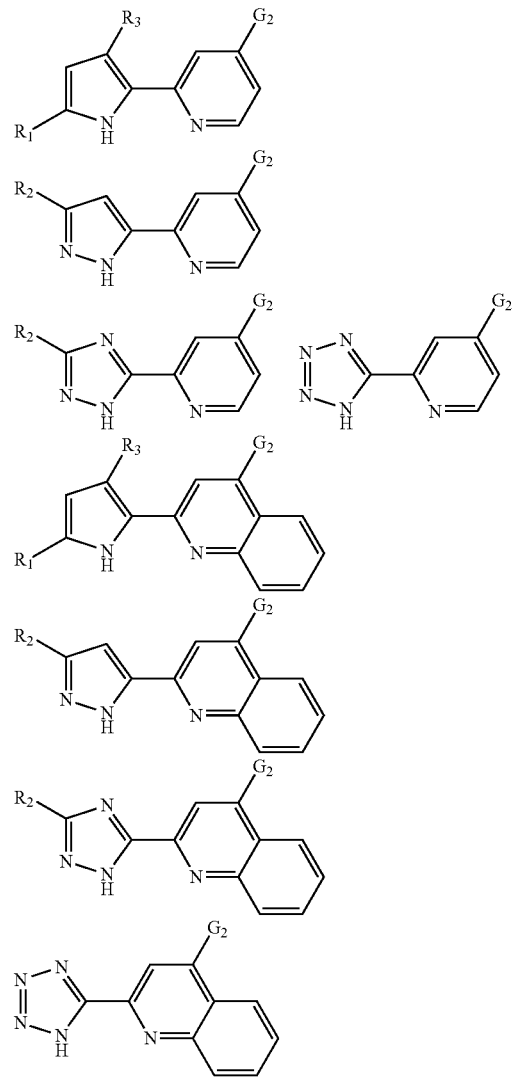

wherein $G_2$ has one of formulae listed below:

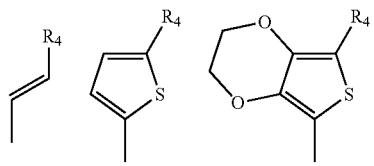

and $L_2$ is a tridentate ligand having a formula listed below:

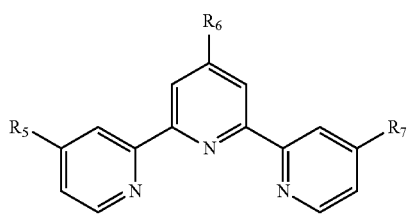

Substituents $R_1$, $R_2$, $R_3$ and $R_4$ of $L_1$ are the same or different and are selected from the group consisting of hydrogen, halogen, amino-group alkyl, alkoxy, alkylthio, alkylamino, halogenated alkyl, phenyl and substituted phenyl group. Substituents $R_5$, $R_6$ and $R_7$ of $L_2$ are the same or different and are selected from the group consisting of carboxylic, carboxylate, sulfonic acid, sulfonate, phosphoric acid and phosphate.

The above-mentioned photosensitizers are suitable to use as sensitizers for fabrication of high efficiency dye-sensitized solar cell.

18 Claims, 2 Drawing Sheets

PANCHROMATIC PHOTOSENSITIZERS AND DYE-SENSITIZED SOLAR CELL USING THE SAME

RELATED APPLICATIONS

This application is a Continuation-In-Part patent application of Ser. No. 12/495,044 filed on Jun. 30, 2009, now abandoned.

BACKGROUND OF THE INVENTION

1. Field of the Invention

The present invention is related to panchromatic photosensitizers and dye-sensitized solar cell using the same, and more particularly to panchromatic photosensitizers and dye-sensitized solar cell using the same with better photoelectric conversion efficiency.

2. Description of the Prior Art

Petrochemical fuel contains nonrenewable energy, which will possibly run out very soon. In addition, burning petrochemical fuel results in excessive $CO_2$ exhausts which not only pollute the air, but also become one of the primary causes of global warming. Therefore, searching for alternative energy supplies to reduce reliance on petrochemical fuels is a subject of great urgency. During the development of green energy, it is found that solar energy is the cleanest, most abundant and requires neither mining nor refinement. Solar energy, therefore, becomes the most notable field among the current development and search for new energy.

The manufacture of a dye-sensitized solar cell (DSSC) is simple and the manufacturing cost is also lower than that of a silicon-based solar cell of prior arts. Therefore, DSSC has been regarded as one of the most promising solar cell technologies following silicon-based solar cells. Because the intrinsic property of photosensitizers directly affects the photoelectric conversion efficiency of a DSSC, the photosensitizers then becomes one of key focus while conducting research on DSSCs.

A N3 dye is a photosensitizer commonly used at present, which comprises the structure shown in Formula (I). However, the absorption spectrum of N3 dye is not well matched to the solar spectrum, which makes N3 dye to respond sluggishly to solar irradiations with wavelengths greater than 600 nm, and cannot be used in this region efficiently.

Formula (I)

Another photosensitizer of prior art is the black dye, which comprises the structure shown in Formula (II). Although black dye somewhat overcomes the drawback of N3 dye, and exhibits spectrum response up to the region of 920 nm, the process involving its synthesis is complicated, the absorption extinction coefficient in the visible region is inferior to those of the typical organic sensitizers, and not to mention of the poor synthetic yield.

Formula (II)

To sum up the foregoing descriptions, the photoelectric conversion efficiency of a DSSC directly depends on the property of a photosensitizer; therefore, developing photosensitizers with decent photoelectric conversion efficiency is an important goal to be achieved.

SUMMARY OF THE INVENTION

The present invention is directed to providing a panchromatic photosensitizers and dye-sensitized solar cell using the same with better spectrum response and photoelectric conversion efficiency.

According to an embodiment, A photosensitizer has a chemical formula represented by Formula (a):

$$ML_1L_2X \qquad \text{Formula (a)}$$

wherein M represents ruthenium atom; X represents a monodentate anion; $L_1$ represents heterocyclic bidentate ligand comprising a structural formula represented by Formula (b) or Formula (c) listed below:

Formula (b)

Formula (c)

wherein $G_1$ has a structural formula represented by Formula (d), Formula (e) Formula (f) or Formula (g) listed bellow:

Formula (d)

Formula (e)

Formula (f)

Formula (g)

$G_2$ has a structural formula represented by Formula (h), Formula (i) or Formula (j) listed below:

Formula (h)

Formula (i)

Formula (j)

and $L_2$ represents a tridentate ligand comprising a structural Formula (k) listed below:

Formula (k)

wherein the substituents $R_1$, $R_2$, $R_3$ and $R_4$ of $L_1$ are the same or different and are selected from the group consisting of hydrogen, halogens, amino-group alkyl, alkoxy, alkylthio, alkylamino, halogenated alkyl, phenyl and substituted phenyl group. Substituents $R_5$, $R_6$ and $R_7$ of $L_2$ are the same or different and are selected from the group consisting of carboxylic acid and counter anion thereof, sulfonic acid and counter anion thereof, phosphoric acid and counter anion thereof.

According to another embodiment, a DSSC comprises a first electrode, a second electrode and an electrolyte. The first electrode comprises a transparent conductive substrate and a porous membrane, wherein the porous membrane, disposed on a surface of the transparent conductive substrate, comprises a semiconductor material and is loaded with the aforementioned photosensitizers. The electrolyte is disposed between the porous membrane and the second electrode.

Other advantages of the present invention will become apparent from the following description taken in conjunction with the accompanying drawings wherein are set forth, by way of illustration and example, certain embodiments of the present invention.

BRIEF DESCRIPTION OF THE DRAWINGS

The foregoing aspects and many of the accompanying advantages of this invention will become more readily appreciated as the same and become better understood by reference to the following detailed descriptions, when taken in conjunction with the accompanying drawings, wherein.

DESCRIPTION OF THE PREFERRED EMBODIMENT

An embodiment of photosensitizers have a chemical formula of Formula (a):

$$ML_1L_2X \qquad \text{Formula (a)}$$

wherein M represents ruthenium atom; X represents a monodentate anion; $L_1$ represents a heterocyclic bidentate ligand having a pyridine or quinoline ligand bonded to a 5-membered nitrogenous ring; and $L_2$ represents a tridentate ligand. In one embodiment, the X may be halide, pseudohalide, carboxylate, carbanion, sulfate, phosphate, thiocyanate or other organic anion. $L_1$ represents a structural formula represented by Formula (b) of pyridine or Formula (c) of quinoline listed below:

Formula (b)

Formula (c)

wherein G₁ is a 5-membered nitrogenous ring, and has a structural formula represented by Formula (d), Formula (e), Formula (f) or Formula (g) listed bellow:

Formula (d)

Formula (e)

Formula (f)

Formula (g)

G2 represents a structural formula represented by Formula (h), Formula (i) or Formula (j) listed below:

Formula (h)

Formula (i)

Formula (j)

and L₂ has a structural formula represented by Formula (k) listed below:

Formula (k)

wherein the substituents $R_1$, $R_2$, $R_3$, $R_4$, $R_5$, $R_6$ and $R_7$ of $L_1$ and $L_2$ may be the same or different, and represent alkyl, alkoxy, alkylthio, alkylamino, halogenated alkyl, phenyl or substituted phenyl group, carboxylic acid or counter anion thereof, sulfonic acid or counter anion thereof, phosphoric acid or counter anion thereof, amino-group, halogens, or hydrogen.

In one embodiment, the substituents $R_1$ and $R_3$ of $L_1$ are the same or different and represent hydrogen, isobutyl or $CF_3$. The substituent $R_2$ of $L_1$ is a member selected from the group consisting of hydrogen, isobutyl, $CF_3$, and a structural formula represented by Formula (l) and Formula (m) listed below:

Formula (l)

Formula (m)

In one embodiment, the substituent $R_4$ of $L_1$ represents an aromatic ring or a functional group of substituted conjugated double bond thereof. Taking Formula (h) for example, $G_2$ represents the following structure:

In one embodiment, the substituents $R_5$, $R_6$ and $R_7$ of $L_2$ may be the same or different, and may represent hydrogen, carboxylic acid, carboxylate, sulfonic acid, sulfonate, phosphoric acid and phosphate. For example, $L_2$ represents the following structure:

EXAMPLE COMPOUNDS

Example photosensitizers of the present invention with the structure of Formula (n) and of a black dye, respectively,

Formula (n)

R may be a members selected from the group consisting of hydrogen, halogens, amino-group alkyl, alkoxy, alkylthio, alkylamino, halogenated alkyl, phenyl and substituted phenyl group. In one embodiment, R in photosensitizer PRT1 is hydrogen; R in photosensitizer PRT2 is $OCH_3$; R in photosensitizer PRT3 is $OC_8H^{17}$; and R in photosensitizer PRT4 is isobutyl.

PRT1-4 may be prepared with general reaction procedures listed following. Commercially available reagents were used without further purification unless otherwise stated.

4-Methyl-2-(3-(trifluoromethyl)-1H-pyrazol-5-yl)pyridine was prepared according to the literature procedures (*Organometallics,* 2003, 22, 4938), while 4,4',4"-triethoxycarbonyl-2,2':6',2"-terpyridine was synthesized via oxidation of 4,4',4"-triethyl-2,2':6',2"-terpyridine, followed by esterification in presence of $H_2SO_4$. $[RuCl_2(p\text{-cymene})]_2$ was prepared by heating $RuCl_3$.hydrate with phellandrene in methanol.

After then, Ru1~Ru4 were prepared by reacting $[RuCl_2(p\text{-cymene})]_2$ with the respective functionalized 2-pyridyl pyrazoles in anhydrous methanol (60° C., 4 hr). The panchromatic Ru(II) terpyridine sensitizers PRT1 to PRT4 were synthesized employing 4,4',4"-triethoxycarbonyl-2,2':6',2"-terpyridine and Ru1~Ru4, followed by treatment with KSCN and then hydrolysis in 1.0 M NaOH solution. The solid product was then taken into a minimum amount of methanol and purified on Sephadex LH-20 column using methanol as the eluent.

Rxn conditions: (i) DGME, 160° C., 8 hr; (ii) KSCN, DMF, 160° C., 6 hr; (iii) NaOH, 24 hr.

Synthesis of (E)-4-styryl-2-(3-(trifluoromethyl)-1H-pyrazol-5-yl)pyridine (L1)

Ligand L1 was synthesized employing a modified literature procedure,[4] in which solid tert-BuOK (1.19 g, 10.56 mmol) was added to a solution of 4-methyl-2-(3-(trifluoromethyl)-1H-pyrazol-5-yl) pyridine (0.30 g, 1.32 mmol) and benzaldehyde (0.4 mL, 3.96 mmol) in anhydrous DMF (100 mL). The resulting mixture was stirred 6 h at 100□ under nitrogen. The solvent was then evaporated, and product was dissolved in water titrated by 2 M HCl until pH 3~4. The insoluble solid was filtered on a sintered crucible and recrystallized from hot ethylacetate (EA), filtered, and washed with methanol to obtain the desired product L1 as a beige solid (0.22 g, 51%).

Other chelates L2~L4 were prepared using identical procedures (Yield: L2 52%; L3 55%; L4 64%).

Preparation of PRT1.

In a typical experiment, Ru1 (100 mg, 0.16 mmol) and 4,4',4''-triethoxycarbonyl-2,2':6',2''-terpyridine (70 mg, 0.16 mmol) were dissolved in a diethylene glycol monoethyl ether solution (DGME, 20 mL). The mixture was heated at 160° C. for 8 h under constant stirring. Solvent was then reduced and product was purified by flash column chromatography using CH2Cl2/methanol (95:5) as the eluent. The resulting product and excess KSCN (155 mg, 1.60 mmol) were then dissolved in DMF solution (15 mL) and refluxed for additional 8 h at 160° C. Next, the solvent was removed under vacuum, and the residue was dissolved into a mixture of 5 mL of acetone and 5 mL of 1.0 M NaOH solution and heated at reflux for 24 h. Finally, the solution was concentrated to one-half of its original volume and neutralized with 2M HCl solution to pH=3 to afford a brown precipitate. This brown product was then taken into a minimum amount of methanol and purified on Sephadex LH-20 column using methanol as the eluent. The main band was collected and solvent was evaporated to dryness. After then, the brown precipitate was washed with deionized water, acetone and diethyl ether in sequence, giving PRT1 as powdery material (32 mg, 24%).

Selected Spectral Data of PRT1:

MS (FAB, 102Ru): m/z 840 (M+2+). 1H NMR (d6-DMSO, 400 MHz) δ: 9.24 (d, 1H, J=5.6 Hz), 9.21 (s, 2H), 9.06 (s, 2H), 8.44 (s, 1H), 8.01 (d, 2H, J=5.6 Hz), 7.95 (d, 1H, J=5.6 Hz), 7.89~7.84 (m, 3H), 7.74 (d, 2H, J=8.0 Hz), 7.52~7.38 (m, 4H), 7.08 (s, 1H). MS (FAB, Ru102): m/z 840 (M+2+). Anal. Calcd for C36H22F3N7O6RuS. 4H2O: C, 47.47; N, 10.76; H, 3.32. Found: C, 47.15; N, 10.39; H, 3.39.

Preparation of PRT2

Dark brown powder of PRT2 (35 mg, 27%) was prepared employing Ru2 (100 mg, 0.15 mmol) with synthetic procedures identical to those for preparing PRT1.

Selected Spectral Data of PRT2:

MS (FAB, 102Ru): m/z 869 (M+1+). 1H NMR (d6-DMSO, 400 MHz) δ: 9.21 (d, 1H, J=5.6 Hz), 9.18 (s, 2H), 9.04 (s, 2H), 8.36 (s, 1H), 8.01 (d, 2H, J=5.6 Hz), 7.86~7.84 (m, 3H), 7.77 (d, 1H, J=16 Hz), 7.64 (d, 2H, J=8.0 Hz), 7.29 (d, 1H, J=16 Hz), 7.05~7.02 (m, 3H), 3.82 (s, 3H). Anal. Calcd for C37H24F3N7O7RuS. 5H2O: C, 46.35; N, 10.23; H, 3.57.

Found: C, 46.61; N, 10.22; H, 3.41.

Preparation of PRT3

Dark brown powder of PRT3 (37 mg, 30%) was prepared employing Ru3 (100 mg, 0.13 mmol) with synthetic procedures identical to those for preparing PRT1.

Selected spectral data of PRT3:

MS (FAB, 102Ru): m/z 968 (M+1+). 1H NMR (d6-DMSO, 400 MHz) δ: 9.22 (s, 2H), 9.17 (d, 1H, J=5.6 Hz), 9.08 (s, 2H), 8.40 (s, 1H), 7.99 (d, 2H, J=5.6 Hz), 7.90 (d, 1H, J=5.6 Hz), 7.84~7.78 (m, 3H), 7.64 (d, 2H, J=8.0 Hz), 7.30 (d, 1H, J=16 Hz), 7.10 (s, 1H), 7.00 (d, 2H, J=8.4 Hz), 4.00 (t, 2H, J=6.4 Hz), 1.70 (m, 2H), 1.40~1.20 (m, 10H), 0.84 (t, 3H, J=6.4 Hz). Anal. Calcd for C44H38F3N7O7RuS. 5H2O: C, 50.00; N, 9.28; H, 4.58. Found: C, 49.92; N, 9.30; H, 4.44.

Preparation of PRT4

Dark brown powder of PRT4 (40 mg, 30%) was prepared employing Ru4 (100 mg, 0.14 mmol) with synthetic procedures identical to those for preparing PRT1.

Selected Spectral Data of PRT4:

MS (FAB, 102Ru): m/z 895 (M+1+). 1H NMR(d6-DMSO, 400 MHz) δ: 9.23 (d, 1H, J=5.6 Hz), 9.18 (s, 2H), 9.04 (s, 2H), 8.40 (s, 1H), 7.98 (d, 2H, J=5.6 Hz), 7.90 (d, 1H, J=5.6 Hz), 7.96~7.82 (m, 4H), 7.67 (d, 2H, J=8.0 Hz), 7.51 (d, 2H, J=8.0 Hz), 7.44 (d, 1H, J=16 Hz), 7.10 (s, 1H), 1.33 (s, 9H). Anal. Calcd for C40H30F3N7O6RuS. CH3OH. 3H2O: C, 50.20; N, 10.00; H, 4.11. Found: C, 50.35; N, 10.30; H, 4.28.

Figure 1:
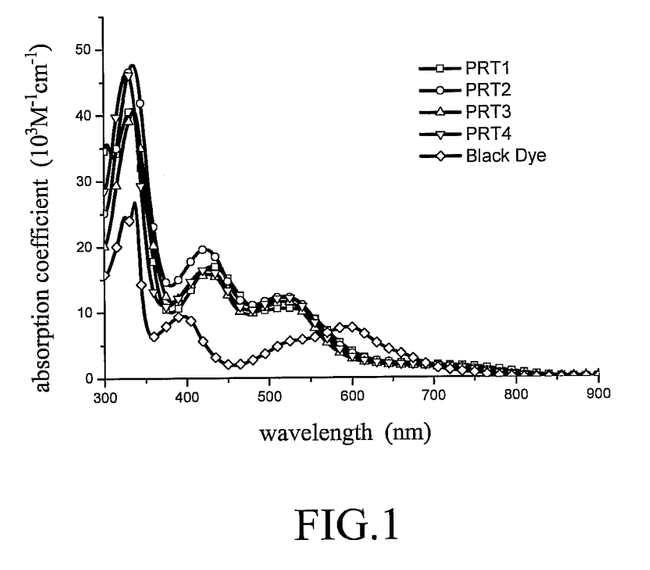
FIG. 1 is a curve diagram illustrating absorption spectrum of a black dye of prior art and photosensitizers according to an embodiment of the present invention, respectively.

Referring to FIG. 1 illustrating an absorption spectrum of PRT1~4 of the present invention and black dye N3 of conventional prior art, it is shown that the value of the light absorption coefficient of photosensitizers of the present invention is better than that of the black dye within a large portion of the wavelength region.

Figure 2:
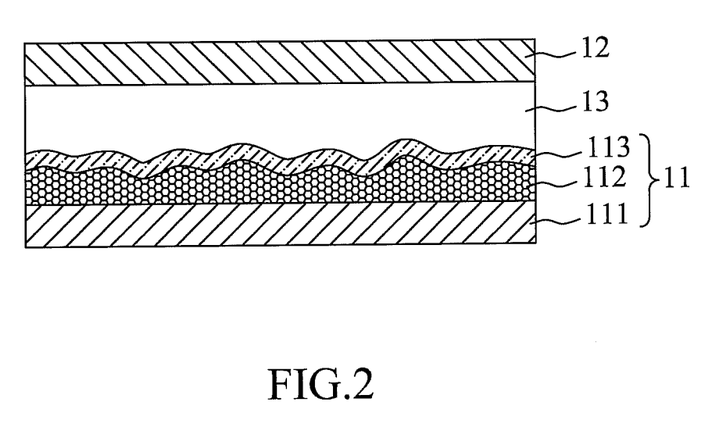
FIG. 2 is a diagram schematically illustrating the structure of a dye-sensitized solar cell according to an embodiment of the present invention.

Referring to FIG. 2, a DSSC of an embodiment of the present invention comprises a first electrode 11, a second electrode 12 and an electrolyte 13. The first electrode 11 comprises a transparent conductive substrate 111 and a porous membrane 112. The porous membrane 112, disposed on a surface of the transparent conductive substrate 111, is loaded with the aforementioned photosensitizers 113. The porous membrane 112 comprises a semiconductor material, such as $TiO_2$. In one embodiment, the transparent conductive substrate 111 comprises F-doped $SnO_2$ glass (FTO glass). The electrolyte 13 is disposed between the porous membrane 112 and the second electrode 12. The structure of the photosensitizers 113 are identical with the aforementioned photosensitizers, therefore, the detail description is skipped herein.

The aforementioned photosensitizers PRT1~PRT4 is utilized to produce a DSSC of the present invention. The characteristics are illustrated in table 1, wherein the first electrode 11 includes photosensitizers PRT1~PRT4, a porous membrane $TiO_2$ and FTO glass; the second electrode 12 comprises a Pt electrode, such as a general glass doped with metal Pt and the alloy thereof, chrome (Cr) for example; the electrolyte comprises a mixture consisting of 0.6 M dimethylpropylimidazolium iodide, 0.1 M $I_2$, 0.1 M LiI, and 0.5 M tert-butylpyridine in acetonitrile.

TABLE 1

| photosensitizer | open-circuit voltage (V) | short-circuit current (mAcm$^{-2}$) | fill factor | η (%) |
|---|---|---|---|---|
| PRT1 | 687 | 20.3 | 0.654 | 9.14 |
| PRT2 | 668 | 21.7 | 0.644 | 9.33 |
| PRT3 | 720 | 20.4 | 0.653 | 9.59 |
| PRT4 | 714 | 21.6 | 0.652 | 10.05 |
| Black Dye | 663 | 18.5 | 0.655 | 8.05 |

According to table 1, the photoelectric conversion efficiency η of a DSSC of the present invention is better than that of a dye-sensitized solar cell with black dye. For example, the photoelectric conversion efficiency η of DSSCs comprising PRT1~PRT4 are 9.14%, 9.33%, 9.59% and 10.05%, respectively. However, the photoelectric conversion efficiency η of a dye-sensitized solar cell employing the black dye is merely 8.05%.

In conclusion, photosensitizers of the present invention are panchromatic photosensitizers and have a better spectrum response in the visible spectral region. A DSSC made of photosensitizers of the present invention has better photoelectric conversion efficiency. In other words, a DSSC of the present invention may comprise a first electrode with thinner porous membrane, which is attributed to the higher absorptivity of these panchromatic photosensitizers, thereby reducing dark current as well as defects during electrode manufacture process so as to increase the open-circuit voltage, and reduce the usage quantities of photosensitizers to lower manufacture cost as well.

While the invention is susceptible to various modifications and alternating descriptions, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. Photosensitizers having a chemical formula represented by Formula (a):

$ML_1L_2X$,  Formula (a)

wherein M represents ruthenium atom;

X represents a monodentate anion;

$L_1$ represents a heterocyclic bidentate ligand having a structural formula represented by Formula (b) or Formula (c) listed below:

Formula (b)

Formula (c)

wherein $G_1$ is a 5-membered nitrogenous ring and has a structural formula represented by a member selected from the group consisting of Formula (d), Formula (e), Formula (f) and Formula (g) listed below:

Formula (d)

Formula (e)

Formula (f)

Formula (g)

wherein $G_2$ has a structural formula represented by Formula (h), Formula (I) or Formula (j) listed below:

Formula (h)

Formula (i)

Formula (j)

and $L_2$ represents a tridentate ligand having a structural formula represented by Formula (k) listed below:

Formula (k)

wherein substituents $R_1$, $R_2$, $R_3$ and $R_4$ of $L_1$ are the same or different and are selected from the group consisting of hydrogen, halogen, amino-group alkyl, alkoxy, alkylthio, alkylamino, halogenated alkyl, phenyl and substituted phenyl group, and substituents $R_5$, $R_6$ and $R_7$ of $L_2$ are the same or different and are selected from the group consisting of hydrogen, carboxylic acid, carboxylate, sulfonic acid, sulfonate, phosphoric acid and phosphate.

2. Photosensitizers according to claim 1, wherein X is a member selected from the group consisting of halide, carboxylate, carbanion, sulfate and phosphate.

3. Photosensitizers according to claim 1, wherein X is thiocyanate.

4. Photosensitizers according to claim 1, wherein the substituents $R_1$ and $R_3$ of $L_1$ are the same or different and are selected from the group consisting of hydrogen, isobutyl and $CF_3$.

5. Photosensitizers according to claim 1, wherein the substituent $R_2$ of $L_1$ is a member selected from the group consisting of hydrogen, isobutyl, $CF_3$ and a structure formula represented by Formula (l) and Formula (m)

Formula (l)

Formula (m)

6. Photosensitizers according to claim 1, wherein the substituent $R_4$ of $L_1$ is an aromatic ring.

7. Photosensitizers according to claim 1, wherein the substituents $R_5$, $R_6$ and $R_7$ of $L_2$ are the same or different and are selected from the group consisting of hydrogen, carboxylic acid, carboxylate, sulfonic acid, sulfonate, phosphoric acid and phosphate.

8. Photosensitizers according to claim 1, having a structure formula represented by formula (n), wherein R is a member selected from the group consisting of hydrogen, halogen, amino-group alkyl, alkoxy, alkylthio, alkylamino, halogenated alkyl, phenyl and substituted phenyl group formula (n)

9. A dye-sensitized solar cell comprising:
a first electrode comprising:
  a transparent conductive substrate; and
  a porous membrane comprising a semiconductor material, disposed on a surface of said transparent conductive substrate, and said porous membrane is loaded with photosensitizers;
a second electrode; and
an electrolyte, disposed between said porous membrane and said second electrode;
wherein said photosensitizers have a chemical formula represented by Formula (a):

$$ML_1L_2X \qquad \text{Formula (a)}$$

wherein M represents ruthenium atom;

X represents a monodentate anion;

$L_1$ represents a heterocyclic bidentate ligand having a structural formula represented by Formula (b) or Formula (c) listed below:

Formula (b)

Formula (c)

wherein $G_1$ is a 5-membered nitrogenous ring and has a structural formula represented by Formula (d), Formula (e), Formula (f) or Formula (g) listed below bellow:

Formula (d)

Formula (e)

Formula (f)

Formula (g)

wherein $G_2$ has a structural formula represented by Formula (h), Formula (I) or Formula (j) listed below:

Formula (h)

Formula (i)

Formula (j)

and

L₂ represents a tridentate ligand having a structural formula represented by Formula (k) listed below:

Formula (k)

wherein substituents $R_1$, $R_2$, $R_3$ and $R_4$ of $L_1$ are the same or different and are selected from the group consisting of hydrogen, halogen, amino-group alkyl, alkoxy, alkylthio, alkylamino, halogenated alkyl, phenyl and substituted phenyl group, and substituents $R_5$, $R_6$ and $R_7$ of $L_2$ are the same or different and are selected from the group consisting of hydrogen, carboxylic acid, carboxylate, sulfonic acid, sulfonate, phosphoric acid and phosphate.

10. A dye-sensitized solar cell according to claim 9, wherein X is a member selected from the group consisting of halide, carboxylate, carbanion, sulfate and phosphate.

11. A dye-sensitized solar cell according to claim 9, wherein X is thiocyanate.

12. A dye-sensitized solar cell according to claim 9, wherein the substituents $R_1$ and $R_3$ of $L_1$ are the same or different and are selected from the group consisting of hydrogen, isobutyl and $CF_3$.

13. A dye-sensitized solar cell according to claim 9, wherein the substituent $R_2$ of $L_1$ is a member selected from the group consisting of hydrogen, isobutyl, $CF_3$ and a structure formula represented by Formula (l) and Formula (m)

Formula (l)

Formula (m)

14. A dye-sensitized solar cell according to claim 9, wherein the substituent $R_4$ of $L_1$ is an aromatic ring.

15. A dye-sensitized solar cell according to claim 9, wherein the substituents $R_5$, $R_6$ and $R_7$ of $L_2$ are the same or different and are selected from the group consisting of hydrogen, carboxylic acid, carboxylate, sulfonic acid, sulfonate, phosphoric acid and phosphate.

16. A dye-sensitized solar cell according to claim 9, wherein said photosensitizers have a structure formula represented by formula (n), wherein R is a member selected from the group consisting of hydrogen, halogen, amino-group alkyl, alkoxy, alkylthio, alkylamino, halogenated alkyl, phenyl and substituted phenyl group formula (n)

17. A dye-sensitized solar cell according to claim 9, wherein said semiconductor is made of $TiO_2$.

18. A dye-sensitized solar cell according to claim 9, wherein said transparent conductive substrate comprises FTO glass.

\* \* \* \* \*